US008206285B2

(12) United States Patent
Blijevsky (10) Patent No.: US 8,206,285 B2
(45) Date of Patent: Jun. 26, 2012

(54) APPARATUS, SYSTEM AND METHOD TO INDICATE IN-VIVO DEVICE LOCATION

(75) Inventor: Alex Blijevsky, Yoqneam Illit (IL)

(73) Assignee: Given Imaging Ltd., Yoqneam (IL)

( * ) Notice: Subject to any disclaimer, the term of this patent is extended or adjusted under 35 U.S.C. 154(b) by 1428 days.

(21) Appl. No.: 10/585,131

(22) PCT Filed: Dec. 29, 2004

(86) PCT No.: PCT/IL2004/001182
§ 371 (c)(1),
(2), (4) Date: May 29, 2007

(87) PCT Pub. No.: WO2005/062716
PCT Pub. Date: Jul. 14, 2005

(65) Prior Publication Data
US 2008/0051633 A1    Feb. 28, 2008

Related U.S. Application Data

(60) Provisional application No. 60/533,262, filed on Dec. 31, 2003.

(51) Int. Cl.
*A61B 1/00* (2006.01)
*A61B 1/04* (2006.01)
*A61B 1/06* (2006.01)
(52) U.S. Cl. ........................................ 600/117; 600/160
(58) Field of Classification Search .................. 382/128; 600/109, 117, 118, 160
See application file for complete search history.

(56) References Cited

U.S. PATENT DOCUMENTS

| 4,278,077 | A | * | 7/1981 | Mizumoto ..................... 600/109 |
| 4,292,961 | A |   | 10/1981 | Kawashima |
| 4,431,005 | A |   | 2/1984 | McCormick |
| 4,656,508 | A |   | 4/1987 | Yokota |
| 5,604,531 | A |   | 2/1997 | Iddan et al. |
| 5,993,378 | A |   | 11/1999 | Lemelson |
| 6,240,312 | B1 |   | 5/2001 | Alfano et al. |
| 7,044,908 | B1 | * | 5/2006 | Montalbo et al. ............. 600/160 |
| 7,251,383 | B2 | * | 7/2007 | Iddan .............................. 385/12 |
| 7,399,274 | B1 | * | 7/2008 | Halla et al. .................... 600/160 |
| 2002/0103417 | A1 |   | 8/2002 | Gazdzinski |
| 2002/0109774 | A1 | * | 8/2002 | Meron et al. .................... 348/74 |
| 2002/0198439 | A1 |   | 12/2002 | Mizuno |
| 2003/0085994 | A1 |   | 5/2003 | Fujita et al. |
| 2003/0117491 | A1 |   | 6/2003 | Avni et al. |
| 2003/0171652 | A1 |   | 9/2003 | Yokoi et al. |
| 2003/0229268 | A1 |   | 12/2003 | Uchiyama et al. |
| 2004/0111011 | A1 |   | 6/2004 | Uchiyama et al. |

(Continued)

FOREIGN PATENT DOCUMENTS
DE     344 0177     11/1984
(Continued)

OTHER PUBLICATIONS

International Search Report, International Application No. PCT/IL2004/001182. Date of mailing Aug. 2, 2005.

(Continued)

*Primary Examiner* — Philip R Smith
(74) *Attorney, Agent, or Firm* — Pearl Cohen Zedek Latzer, LLP (57) ABSTRACT

A system, apparatus and method may indicate in-vivo device (10) location within a body utilizing for example illumination irregularities for calculation of location. There may be provided with an in-vivo imaging device (24) a set of dedicated illumination sources (43) and a set of detectors (30) located on an in-vivo device, such as a swallowable capsule (10).

7 Claims, 4 Drawing Sheets

U.S. PATENT DOCUMENTS

| | | | |
|---|---|---|---|
| 2004/0204630 A1* | 10/2004 | Gilad | 600/160 |
| 2004/0210131 A1 | 10/2004 | Fukuda et al. | |
| 2005/0074151 A1* | 4/2005 | Chen et al. | 382/128 |
| 2006/0155174 A1* | 7/2006 | Glukhovsky et al. | 600/301 |

FOREIGN PATENT DOCUMENTS

| | | |
|---|---|---|
| JP | 1992-144533 | 5/1992 |
| WO | WO 01/65995 | 9/2001 |
| WO | WO 2004/082472 | 9/2004 |

OTHER PUBLICATIONS

Localization of a wireless capsule endoscope in the GI Tract, Gastrointestinal Endoscopy 2001;53:AB126.

Park, et al., "A Technique for Localization of Biomedical Telemetry Sensor in Human Body", Proceedings of the International Sensor Conference 2001, Seoul, Korea.

* cited by examiner

APPARATUS, SYSTEM AND METHOD TO INDICATE IN-VIVO DEVICE LOCATION

PRIOR APPLICATION DATA

The present application is a national phase application of International Application PCT/IL2004/001182, entitled "APPARATUS, SYSTEM AND METHOD TO INDICATE IN-VIVO DEVICE LOCATION" filed on Dec. 29, 2004, which in turn claims priority from U.S. provisional application Ser. No. 60/533,262, filed on Dec. 31, 2003, entitled "APPARATUS, SYSTEM AND METHOD TO INDICATE IN-VIVO DEVICE LOCATION", all of which are incorporated by reference in their entirety.

FIELD OF THE INVENTION

The present invention relates to in-vivo devices and systems, methods, and apparatuses that help locate in-vivo devices inside a body.

BACKGROUND OF THE INVENTION

Known devices may be helpful in providing in-vivo imaging, diagnosis, treatments etc. For example, autonomous in-vivo devices, such as swallowable capsules, may move through a body lumen, collecting data as they move along. This data may be transmitted to an external reception device, and processed by a processing unit, to help, for example, determine in-vivo parameters. It would be highly advantageous to have a system or method to help indicate the location of an in-vivo device.

SUMMARY OF THE INVENTION

There is provided, in accordance with some embodiments of the present invention, an apparatus, system, and method for indicating in-vivo device location within a body. According to one embodiment of the invention there may be provided, in an in vivo device at least an imager, a primary illumination source to provide illumination for the imager, a dedicated illumination source, a detector to collect light and a processor to, based on signals from the detector, determine a location of the in-vivo device.

According to a further embodiment of the invention there is provided a method for indicating in-vivo device location within a body. The method according to one embodiment of the invention comprises the steps of transmitting light, optionally from behind an optical window in an in-vivo sensing device, receiving reflected light by a detector and determining the location of the device.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements throughout the serial views.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Some embodiments of the present invention are directed to a swallowable in-vivo device that may be used for recording in vivo data, for example from the entire or part of the length of the gastrointestinal (GI) tract, and transmitting recorded data to a receiving and/or processing unit. Other embodiments need not be swallowable or autonomous, and may have other shapes or configurations. According to some embodiments the in vivo device may include an image sensor, however, other sensors may be used. The system and method of the present invention may be used with or in an imaging system such as that described in International Publication Number WO 01/65995, entitled "A Device and System for In-Vivo Imaging", international publication date Sep. 13, 2001, international filing date Mar. 8, 2001. A further example of an imaging system with which the system and method of the present invention may be used is described in U.S. Pat. No. 5,604,531 to Iddan et al., entitled "In-Vivo Video Camera System", filed on Jan. 17, 1995. Both these publications are assigned to the common assignee of the present application and are hereby incorporated by reference. Furthermore, receiving, storage, processing, and/or display systems suitable for use with embodiments of the present invention may be similar to embodiments described in WO 01/65995 and/or in U.S. Pat. No. 5,604,531. Of course, devices, systems, structures, functionalities, and methods as described herein may have other configurations, sets of components and processes etc.

Embodiments of the device are typically autonomous and are typically self-contained. For example, the device may be capsule shaped or otherwise shaped, e.g., in a peanut shape, where all the components are substantially contained within a container or shell, and where the device does not require any wires or cables to, for example, receive power or transmit information. The device may communicate with an external receiving and display system to provide display of data, control, or other functions. For example, power may be provided by an internal battery or a wireless receiving system. Other embodiments may have other configurations and capabilities.

For example, components may be distributed over multiple sites or units. Control information may be received from an external source.

Figure 1:
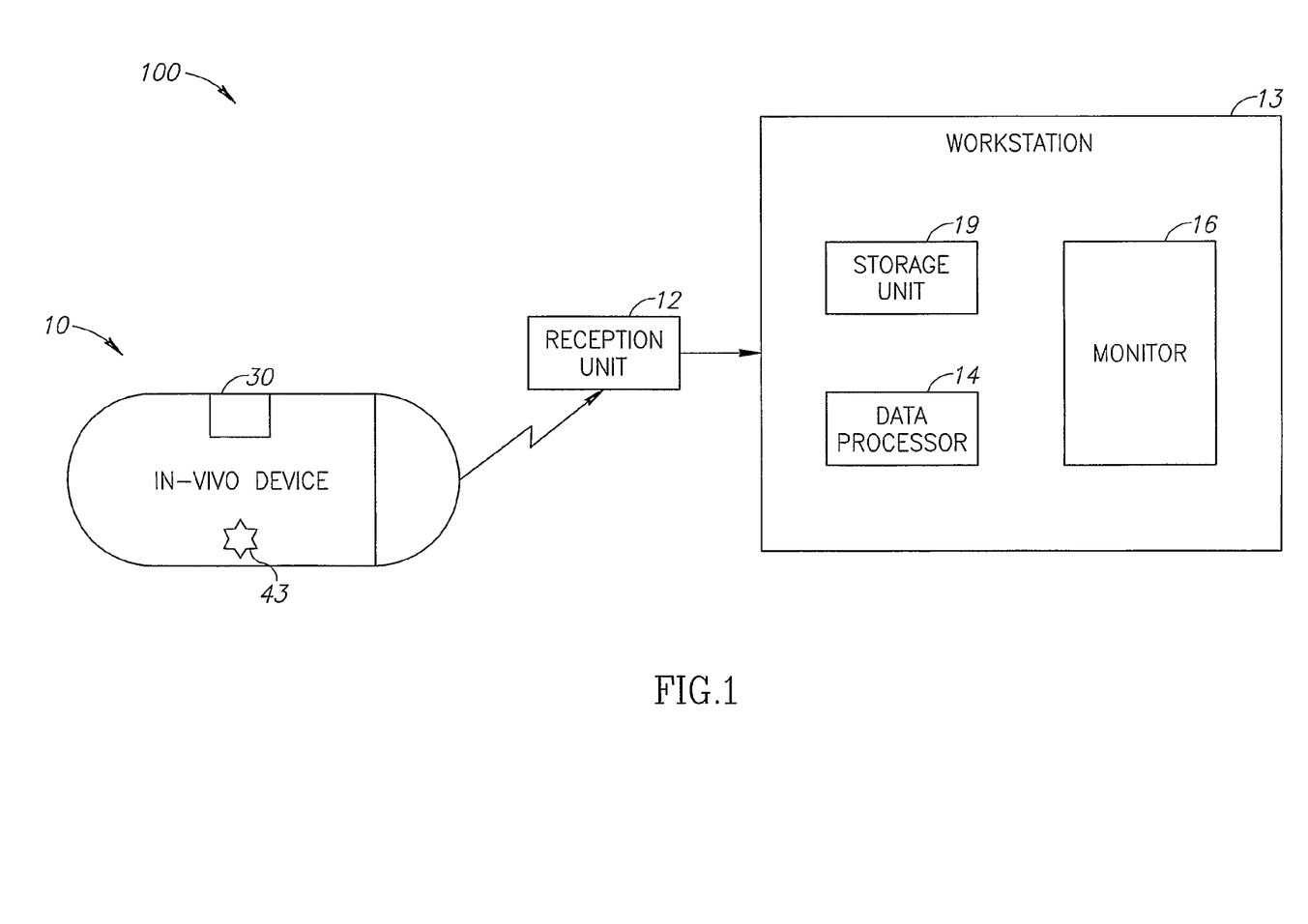
FIG. 1 is a schematic illustration of an in vivo device and imaging system according to one embodiment.

Reference is now made to FIG. 1, which is a schematic illustration of an in-vivo imaging system 100, according to an embodiment of the invention. System 100 may include, for example, an in-vivo device 10, which may be, for example, a swallowable capsule. Device 10 may be an imaging device, and/or may include non-imaging capability.

According to one embodiment of the present invention, in-vivo device 10 may include, for example, one or more detection units and/or detectors 30, for example illumination detectors. According to some embodiments of the present invention, in-vivo device 10 may include a set of energy output units or sources such as one or more dedicated illumination sources 43. System 100 may include a data reception unit 12 to receive at least in-vivo device data, and a data processor 14 to process at least in-vivo device data. System 100 may further include a displaying apparatus, such as a monitor 16, to display at least in-vivo device data. For example, data reception unit 12 may receive the data from in-vivo device 10, and may thereafter transfer the data to a data processor 14, and optionally a data storage unit 19. The data may be displayed on monitor 16. Data reception unit 12 may be separate from the processing unit 14 or combined with it. Data processor 14 may be, for example, associated with a personal computer or workstation, and may include, for example, a processor memory etc. Data processor 14 may be configured for real time processing and/or for post processing to be viewed or otherwise displayed at a later date. Units 14, 16 and 19 may be integrated into a single unit, for example a workstation 13, or any combinations of the various units may be implemented. Of course, other suitable components may be used.

Device 10 as depicted in FIG. 1 may be capsule shaped, and may be easily inserted (e.g., by swallowing) and passively passed through the entire GI tract, pushed along, for example, by natural peristalsis. Nonetheless, it should be appreciated that device 10 may be of any shape and size suitable for being inserted into and passing through a body lumen or cavity, such as spherical, oval, cylindrical, etc. or other suitable shapes. Furthermore, device 10 or various embodiments that may include at least some components of device 10 may be attached or affixed on to an instrument that is inserted into body lumens and cavities, such as, for example, on an endoscope, laparoscope, stent, needle, catheter etc.

Figure 2:
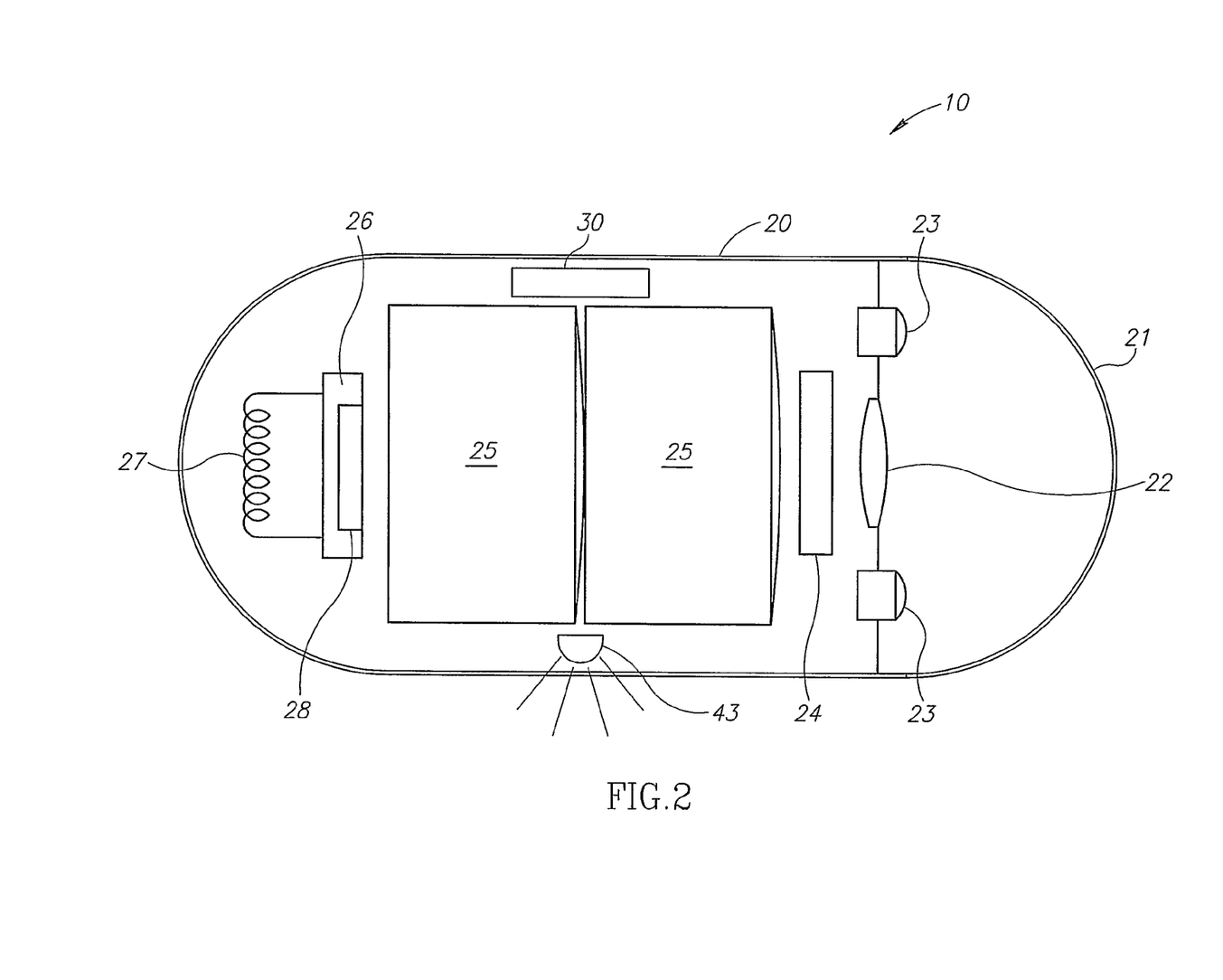
FIG. 2 is a schematic illustration of an in vivo device according to some embodiments of the present invention.

Reference is now made to FIG. 2, which is a schematic illustration of an in-vivo device, e.g., a swallowable capsule, according to an embodiment of the present invention, which may be adapted to indicate in-vivo device location within a body. According to one embodiment of the present invention, device 10 may include at least one illumination source, for example one or more primary illumination source(s) 23 such as, a white Light Emitting Diode (LED) and/or an Organic LED (OLED) or any other suitable illumination source for illuminating a body lumen; an imager 24, such as, for example a CMOS imaging camera, a Charge Coupled Device (CCD), or any other suitable imaging device; and an optical system 22 including, for example, a lens, which may focus images onto imager 24. According to some embodiments of the present invention, primary illumination source 23 may provide illumination for the imager 24 and/or may illuminate the inner portions of a body lumen through at least one optical dome or window 21. Device 10 may include a transmitter 26 and an antenna 27 for transmitting signals and/or data received from at least imager 24, and a power source 25, such as, for example, a battery (e.g., a silver oxide battery, etc.) or any other suitable power source that may provide power to the electrical elements of device 10.

According to one embodiment of the present invention, device 10 may include a processor and/or controller 28, for example, an ASIC (Application Specific Integrated Circuit) controller, optionally located within transmitter 26, or within any other component of device 10, to enable processing of recorded data and/or to control device 10. Optionally, in one embodiment, transmitter 26 may include a processing unit or processor or controller, for example, to process signals and/or data generated by imager 24 and or detector 30. The optional processing unit may include, for example, a Central Processing Unit (CPU), a Digital Signal Processor (DSP), a microprocessor, a controller, a chip, a microchip, a controller, circuitry, an Integrated Circuit (IC), an ASIC, or any other suitable multi-purpose or specific processor, controller, circuitry or circuit. Device 10 may include a processing unit separate from transmitter 26 that may, for example, contain or process instructions. Transmitter 26 may operate using radio waves, but in some embodiments, such as those where the device 10 is or is included within, for example, an endoscope, transmitter 26 may transmit via, for example, a wire-based channel or another suitable method. In-vivo device 10 may include an imaging system for obtaining images from inside a body lumen, such as the GI tract, or may have no such imaging system. Other structures, components, and/or combinations of components may be used.

According to some embodiments of the present invention, device 10 may include one or more detectors 30, for example illumination or light level detectors. Detectors 30 may be dedicated to non-imaging tasks, such as detecting light levels rather than collecting images. According to one embodiment of the present invention the detectors 30 may be placed, for example, at a location(s) on, embedded in, or towards the outer shell of device 10, or at any other location of device 10, such that a portion of illumination generated by primary light source(s) 23 or other light source(s) and reflected or remitted from in-vivo objects or lumen walls etc. to detector 30 may not be received through optical dome or window 21, for example, the device's optical window e.g. the device's primary optical window, and thus not fall on imager 24. For example, according to one embodiment of the present invention, when the sides of device 10, in the vicinity of detector 30, are close to or touching the cavity or lumen walls (e.g., device 10 is passing through a relatively small, typically tube-like cavity), light emitted by primary illumination sources 23 may not substantially illuminate lumen walls or in-vivo objects in the area from which light may be reflected to detector 30. When the sides of device 10, in the region of detector 30, are not substantially close to the cavity or lumen walls (e.g., device 10 is passing through a relatively large cavity), light emitted by the primary illumination sources 23 may illuminate lumen walls or in-vivo objects in the area from which light may be reflected to detector 30. In this way detector 30 may detect light from the primary illumination sources 23 when device 10 is traversing a relatively large lumen, and may not detect substantial light from the primary illumination source 23 when device 10 is traversing a relatively small lumen. Thus detector 30 is preferably not adjacent to illumination sources.

According to one embodiment of the present invention, device 10 may include one or more dedicated illumination source(s) 43, which may be placed, for example, at one or more locations towards the outer shell of device 10. According to some embodiments of the present invention, the dedicated illumination sources 43 may be placed on the sides or at any other location of device 10, such that light generated by illumination source 43 and reflected from in-vivo objects or lumen walls etc. to detector 30 is not substantial when device 10 is passing through, for example, a narrow cavity. In one embodiment, while primary illumination source(s) 23 are behind the optical window or dome 21, along with imager 24, dedicated illumination source(s) 43 and detector(s) 30 are not behind the optical window or dome 21. Thus imager 24 collects images using light from illumination source 23, and the level of light incident on detector 30 varies based on whether detector 30 and/or dedicated illumination source 43 is covered by, e.g., a lumen wall.

Other types of energy output units or sources, other than the dedicated illumination sources 43, may be used. For example, one or more energy sources outputting, for example, acoustic energy or electric energy may be used; if so, corresponding appropriate energy receiving units (e.g., electrodes, acoustic detectors, etc.) may be used. While in one embodiment the energy producing units and energy receiving units are paired (e.g., dedicated illumination source 43 is paired with detector 30), in other embodiments, such pairings need not be used. For example, one energy unit such as a dedicated illumination source may provide illumination, and a set of detectors placed an appropriate distance apart may receive reflection data.

In an alternate embodiment other light sources, separate from a primary light source (e.g., light sources 23), may operate via optical dome or window 21, but may be configured to not be primary illumination sources. One or more detector(s), for example, imager 24, may be located in any suitable location in device 10 so as to receive illumination data from dedicated illumination sources 43 after being reflected off an in-vivo object or lumen wall etc. (and possibly passing through window 21). According to one embodiment of the present invention, imager 24 may be used for other imaging functions for device 10, or may be wholly or partially dedicated to detection of illumination generated by dedicated illumination source(s) 43. For example, imager 24 may include a certain number of pixels in, for example, an unused or little used portion of an imager. Alternately, according to some embodiments of the present invention imager 24 may be placed closer to the dedicated illumination sources 43, or to a path of light from the dedicated illumination source(s) 43.

In some embodiments device 10 may have one or more optical windows 21, with associated imaging or other suitable components. According to one embodiment of the present invention, detector 30 may enable determination of ambient light in a lumen, resulting, for example, from the reflection of light from the primary light sources 23 off a lumen wall. According to some embodiments of the present invention, detector 30 may be, for example, a CMOS camera, a CCD, a photodiode, or any other suitable light detector or imaging device. Detector 30 may be similar to imager 24, and in some embodiments detector 30 may replace imager 24. In further embodiments, an imager such as imager 24, may both provide in-vivo images and perform the functions of detector 30. In some embodiments, detector 30 may be a simple light level meter (e.g., a photodiode), not recording images.

According to some embodiments of the present invention, when device 10 travels in-vivo through a relatively small diameter lumen, for example, such that the lumen walls are in close vicinity to the shell 20, which envelopes in-vivo device 10, and in close vicinity to detector 30, detector 30 may receive minimal or negligible reflected light or other electromagnetic information from illumination sources such as the primary illumination source(s) 23 and/or the dedicated illumination source(s) 43. When device 10 travels through or into a relatively large diameter lumen (e.g., the stomach relative to the esophagus, the large intestine relative to the small intestine), or passes into or out of a relatively large space (e.g., into or out of the body itself) for example, such that a lumen wall is not necessarily in close vicinity to shell 20, light from primary illumination source(s) 23 and/or the dedicated illumination source(s) 43 that reflects off the lumen walls (e.g., ambient light) may be wholly or partially received by detector 30.

According to some embodiments of the present invention, the movement of device 10 from a large space to a relatively small space may affect the amount of electromagnetic energy recorded by detector 30. Thus, after not having received reflected light at detector 30 (or receiving a certain amount of light, or light below a threshold), when detector 30 receives light (or receives a different amount of light, or light above a predetermined threshold), for example, data from detector 30 may trigger transmission of a signal to indicate that device 10 is located within a substantially larger diameter lumen. Additionally or alternatively, according to some embodiments of the present invention, data from detector 30 may trigger (for example via a separate controller or processor) transmission of a signal to indicate that device 10 is located within a substantially smaller diameter lumen when, for example, detector 30 stops receiving light or starts receiving substantially less light.

In other embodiments, after detecting a status change in light received by detector 30, for example, after receiving substantially more light to detector 30, and/or receiving less or no light to detector 30, a controller (e.g., controller 28, transmitter 26 if it includes control or processing capability, or another suitable unit) may receive and process the data from detector 30, and may trigger one or more events to occur within device 10, by one or more components of device 10. According to some embodiments of the present invention, controller 28 may be the main processor/controller of in-vivo device 10 or it may be dedicated to detector 30 or to any other sub-systems. According to one embodiment of the present invention, another processing unit, such as transmitter 26, may be associated with detector 30. For example, controller 28 or another processing device may initiate sending of a signal and/or execution of an event in response to a status change in the light received by detector 30. In other embodiments, an imager such as imager 24 may collect light level data. According to one embodiment of the present invention, the imager 24 may indicate movement of device 10 from one area to another, for example from a relatively small diameter lumen into a larger diameter lumen affects by, for example measuring the amount of light received by imager, and/or illumination changes.

According to some embodiments of the present invention, detector 30 may enable provision of an indication as to an in-vivo device location in a body, for example based on different measurement as described above. For example, detector 30 or information received from detector 30, such as light level information, may indicate when device 10 has passed out of the small intestine (e.g., where the walls may be in close vicinity to device 10) and has moved into the large intestine, which has a larger diameter. Similarly, information from detector 30 may, for example, provide an indication as to when device 10, for example, has passed out of the stomach and moved on to the small intestine, or has left the esophagus and moved into the stomach etc.

Examples of events that may be triggered following an indication by device 10 of a location change of device 10 may include, for example, commanding device 10 to transmit images after device 10 provides an indication that it has reached the colon; instructing device 10 to deliver medication or take samples etc. at one or more selected times and/or locations; instructing device 10 to start or finish events due to the indication given; instructing device 10 to change operation mode, etc. Other examples may include, for example, changing the focus of imager 24, changing the lighting from light sources 23 and/or 43, releasing a chemical, starting data transmission, shutting down or pausing imaging or other function, and initiating or ceasing in-vivo sensing by one or more sensing devices (e.g., pH sensor, temperature sensor, etc.). Other suitable mode changes or operations may take place. For example, device 10 may be controlled according to the location indication, thereby enabling energy saving for device 10, for example, by initiating events or ceasing events according to the progress of device 10 through the GI tract. Other events or operations may be triggered.

According to some embodiments of the present invention, detector 30 may transmit signals relating to light detection to controller 28, for example, ASIC controller, or any suitable data processing unit. Controller 28 may receive these signals and determine from the received signals, for example, by comparing the signals with prior received signals, whether or not there has been a status change in the light received by detector 30, for example, according to a pre-determined threshold. In the case where a status change in light received by detector 30 has been determined (e.g., substantially more light is received, or substantially less light is received), controller 28 may trigger a signal indicating, for example, a location change of device 10. The signal may be sent to any device 10 components, or may be transmitted to one or more receiving units outside device 10, by, for example, transmitter 26. According to one embodiment of the present invention, controller 28 may additionally or alternatively trigger an event, for example, in device 10, or in an external device such as, for example, data processor 14. According to one embodiment of the present invention, light status change may be determined according to the changes in quantity and/or quality of light received to detector 30. In an alternate embodiment data such as raw data or filtered data from detector 30 or another suitable light detection component (e.g., an imager) may be transmitted to an external device (e.g., data processor 14), where a status change such as movement between different sized lumens may be determined. Such data may be transmitted, for example, via transmitter 26.

Figure 3A:
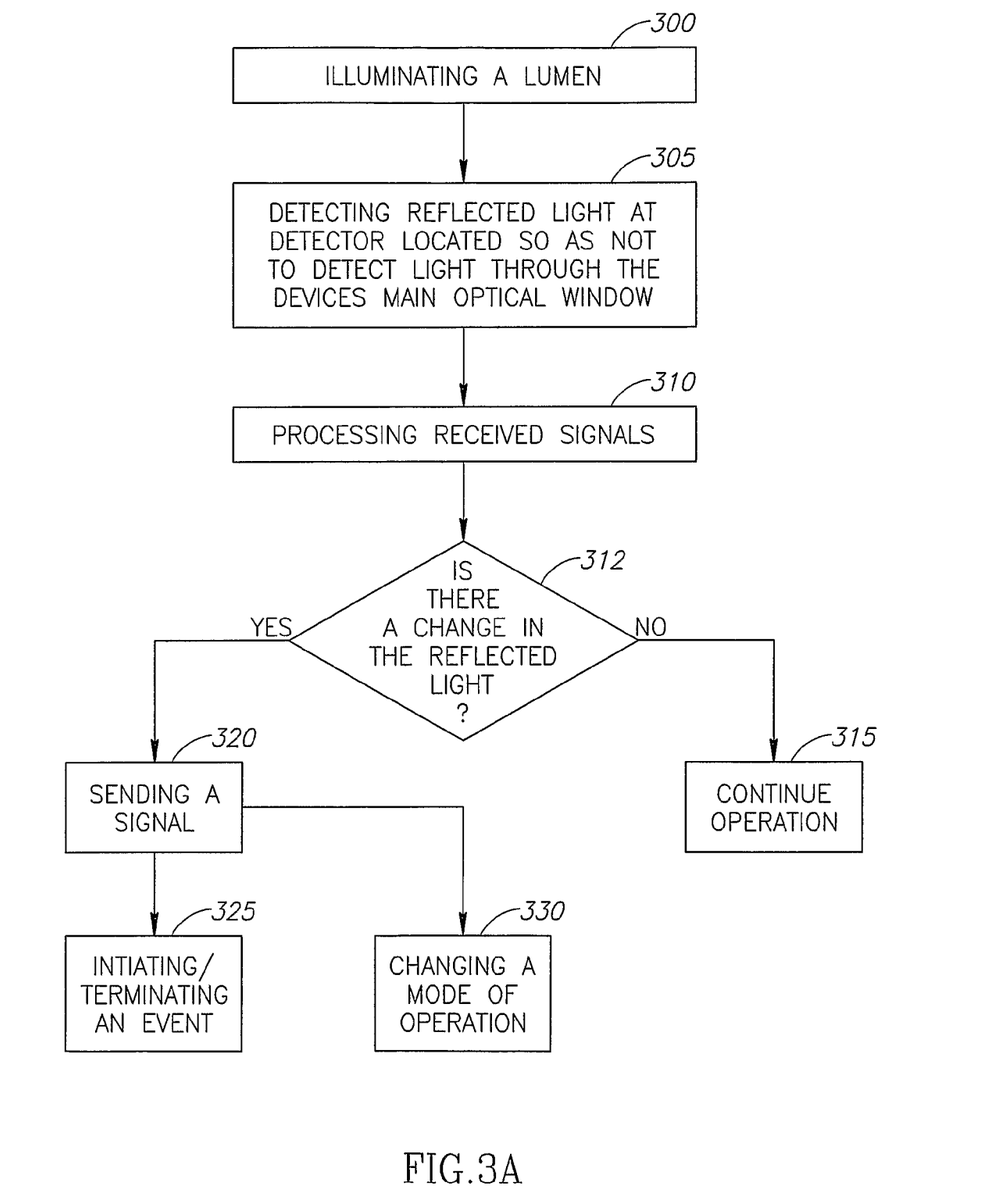
FIGS. 3A and 3B are flow charts illustrating methods for in-vivo location indication according to some embodiments of the present invention.

Reference is now made to FIG. 3A, which is a flow chart depicting a method for indicating in-vivo device location within a body, according to some embodiments of the present invention. At block 300, a lumen may be illuminated for example by transmitting light from behind an optical window in an in-vivo sensing device, for example from a primary light source 23. At block 305, light reflected to one or more detectors, for example positioned so as not to detect light through the device's main optical window, may be detected. At block 310, signals received from reflected light may be processed. At block 312 it may be determined whether there has been a change or substantial change in the quality and/or quantity of light received by the detector. At block 315 if there is no substantial change in the quality and/or quantity of light received, as determined according to a pre-determined threshold, the in-vivo device may continue functioning as before. At block 320, if there is a change in the quality and/or quantity of light received, for example as determined according to a pre-determined threshold, the in-vivo device may send a signal to a reception unit, processing unit, and/or a user/operator etc. At block 325, if there is a change in the quantity and/or quality of light received, for example, as determined according to a pre-determined threshold, a user or operator of the in-vivo device may initiate and/or terminate one or more events. Additionally or alternatively, at block 330, if there is a change in the quantity and/or quality of light received, for example, as determined according to a pre-determined threshold, a user or operator of the in-vivo device may change a mode of operation. The initiating or terminating of events, and/or changing of operation mode etc. of the in-vivo device may be implemented by a user or operator of the device, or by the device processor or alternative controller. Any combination of the above steps may be implemented. Further, other steps or series of steps may be used. For example, the steps of determining if a light pattern or level has changed to determine a position change may be performed by a processor external to the body based on signals transmitted from the in-vivo device.

According to another embodiment of the present invention, at block 312 it may be determined if the light being detected is above or below a predetermined threshold. According to this determination the device or components of the device may be made to continue operation (block 315) or to send a signal (block 320) or to initiate or terminate an event (block 325) or change a mode of operation (block 330) or any other suitable operation according to embodiments of the invention. The in-vivo device, for example, without the interaction of a user or operator, may implement these operations or other suitable operations. For example, an imaging device, such as described above, may be ingested, swallowed, or otherwise inserted by a patient. Upon swallowing, while the device is in the patient's esophagus and relatively little light (e.g., under a predetermined threshold) reaches the devices detector the imager of the device may be imaging at a high frame rate. When the imaging device reaches the patient's stomach a relatively large amount of light may be detected by a detector in the device and as a result the frame rate may be lowered. Various other mode changes may occur. When the device enters the small intestine from the stomach the amount of light detected by the detector may again be below a predetermined threshold and as a result the main illumination of the device may be intensified. Other steps and operations are possible.

Figure 3B:
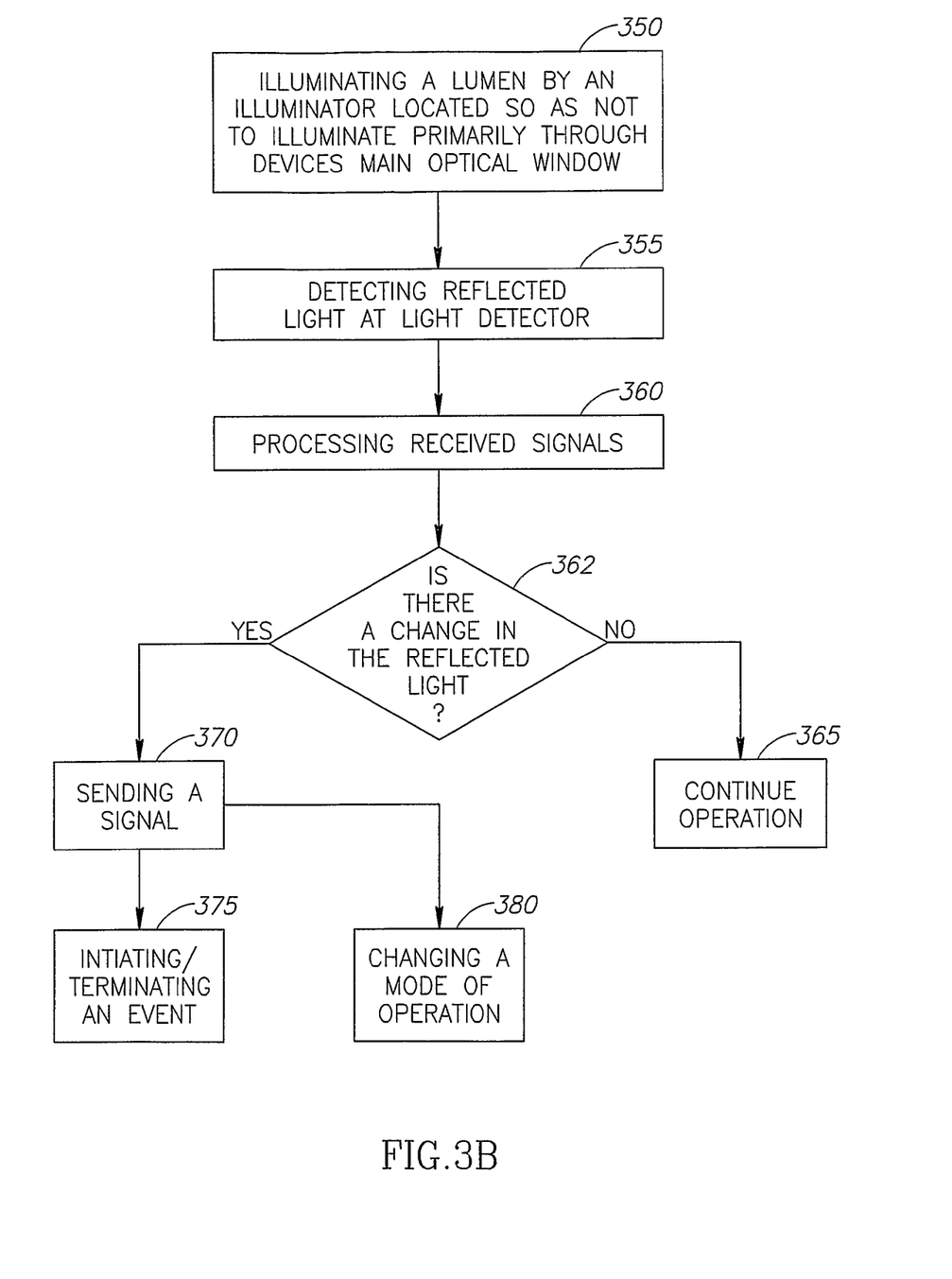

Reference is now made to FIG. 3B, which is a flow chart depicting a method for indicating in-vivo device location within a body, according to some embodiments of the present invention. Embodiments of the method may be, for example implemented using at least one illumination source positioned on the sides of device 10 or at any other location of device 10, such that light discharged for example through the dedicated illumination source(s) 43 which illuminates objects (for example, lumen walls), may not be reflected off the object or lumen wall and may not be detected by, for example imager 24, when device 10 is traversing a small diameter lumen. However, the method may be implemented using other in-vivo devices having other suitable structures.

At block 350, a lumen may be illuminated for example by transmitting light from one or more illumination sources such as the dedicated illumination source(s) 43 which, for example may be positioned at the sides of an in-vivo device or otherwise suitably positioned. At block 355, the light reflected off the in-vivo objects or lumen walls etc. to one or more light detectors, for example imager 24, may be detected. At block 360, signals received from reflected light may be processed, for example, by processor 28 or other suitable processing units. At block 365, if there is no substantial change in the quality and/or quantity of light received, as determined according to a pre-determined threshold, the in-vivo device and/or an external processing or receiving system may continue functioning as before. At block 370, if there is a change in the quality and/or quantity of light received, for example as determined according to a pre-determined threshold, a user or operator of the in-vivo device may send a signal to a reception unit, processing unit, and/or a user/operator etc. In the case where a user and/or operator receive a signal or data, the user and/or operator may provide an instruction to initiate or terminate an event in the in-vivo device or in other system components.

At block 375, if there is a change in the quality and/or quantity of light received, for example, as determined according to a predetermined threshold, a user or operator of the in-vivo device may initiate and/or terminate one or more events. Additionally or alternatively, at block 380, if there is a change in the quality and/or quantity of light received, for example, as determined according to a pre-determined threshold, a user or operator of the in-vivo device may change a mode of operation of the device and/or an external system. The initiating or terminating of events, and/or changing of operation mode etc. of the in-vivo device may be implemented by a user or operator of the device, or by the device processor or alternative controller. Any combination of the above steps may be implemented. Further, other steps or series of steps may be used. For example, the steps of determining if a light pattern or level has changed to determine a position change may be performed by a processor external to the body based on signals transmitted from the in-vivo device.

According to another embodiment at block 362 it may be determined if the light being detected is above or below a predetermined threshold. According to this determination the device may be made to continue operation (block 365) or to send a signal (block 370) or to initiate or terminate an event (blocks 375 and 380 respectively) or any other operation according to embodiments of the invention. The in-vivo device, for example, without the interaction of a user or operator, may implement these operations or other suitable operations.

According to some embodiments of the present invention, the in-vivo motion detection may be implemented using at least one detector 30 and at least one dedicated illumination source 43; both being positioned substantially separately from the primary illumination source(s) 23 and the imager of the in-vivo device 10. For example, the detector(s) 30 may be placed so as to detect light that is substantially reflected from an in-vivo object or lumen wall etc., the light having emanated from the dedicated illumination source 43. For example, the dedicated illumination unit(s) 43 may be placed so as to generate light that substantially illuminates an in-vivo object or lumen wall etc. not using optical window 21 (e.g., detector may be located on one or more sides of in-vivo device 10). In this way, for example, in a small diameter lumen, the detector may not receive light or may only receive light under a certain threshold, while in a large lumen, the detector may receive light above a certain threshold.

According to some embodiments motility of the GI tract may be determined by measuring received light, according to embodiments of the invention. Typically, contractions of the lumen wall around the device may result in a reduced amount of light remitted from the lumen wall or otherwise changed quantity or quality of remitted light. According to some embodiments fluctuations in received light may indicate the motility pattern of the lumen being examined.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. An in-vivo system comprising:
   an autonomous in vivo device for traversing lumens having different diameters, said device comprising:
   an outer shell comprising an optical window;
   an illumination source and an imager positioned behind an optical window, the imager imaging via the optical window and the illumination source providing illumination via the optical window; and
   a light detector receiving reflected light not via the optical window;
   a processor to determine the movement of the in-vivo device between a first lumen having a first diameter to a second lumen having a second diameter wherein the lumen walls are closer to the outer shell when the device is in the one of the first lumen and the second lumen, based on the light detector detecting less light in the lumen where the lumen walls are closer to the outer shell.

2. The system according to claim 1, wherein the first diameter is a relatively small diameter lumen and wherein the second diameter is a larger diameter.

3. The system according to claim 1, wherein said detector is selected from the group consisting of: a CMOS, a CCD and a photodiode.

4. The system according to claim 1, comprising a controller, wherein said controller is configured to receive signals from said detector and to trigger an event to occur within said in-vivo device.

5. The system according to claim 1 comprising a transmitter.

6. The system according to claim 1, wherein the in-vivo device is a swallowable in-vivo device traversing the gastrointestinal tract and wherein the lumens are organs of the gastrointestinal tract.

7. The system according to claim 1, wherein the light detector is placed at a location on said outer shell.

* * * * *